(12) United States Patent
Pandia

(10) Patent No.: US 11,986,204 B2
(45) Date of Patent: *May 21, 2024

(54) ULTRASONICALLY FLARED MEDICAL-DEVICE COMPONENTS AND METHODS THEREOF

(71) Applicant: C.R. Bard, Inc., Franklin Lakes, NJ (US)

(72) Inventor: Deepa Pandia, Phoenix, AZ (US)

(73) Assignee: C.R. Bard, Inc.

(*) Notice: Subject to any disclaimer, the term of this patent is extended or adjusted under 35 U.S.C. 154(b) by 142 days.

This patent is subject to a terminal disclaimer.

(21) Appl. No.: 17/722,700

(22) Filed: Apr. 18, 2022

(65) Prior Publication Data

US 2022/0240972 A1 Aug. 4, 2022

Related U.S. Application Data

(63) Continuation of application No. 16/346,694, filed as application No. PCT/US2017/061462 on Nov. 14, 2017, now Pat. No. 11,331,114.

(60) Provisional application No. 62/427,146, filed on Nov. 28, 2016.

(51) Int. Cl.
| A61B 17/32 | (2006.01) |
| A61B 17/00 | (2006.01) |
| A61B 17/3207 | (2006.01) |
| A61M 25/00 | (2006.01) |

(52) U.S. Cl.
CPC ........ *A61B 17/320068* (2013.01); *A61B 17/320725* (2013.01); *A61B 2017/00526* (2013.01); *A61B 2017/320072* (2013.01); *A61M 25/0074* (2013.01)

(58) Field of Classification Search
CPC ........ A61B 17/320068; A61B 17/3207; A61B 17/320725; A61B 17/320758; A61B 2017/320069; A61B 2017/320071; A61B 2017/320072; A61B 2017/320073; A61B 2017/320078; A61B 2017/320766; A61B 2017/320775
See application file for complete search history.

(56) References Cited

U.S. PATENT DOCUMENTS

| 5,135,531 A | 8/1992 | Shiber |
| 5,197,971 A | 3/1993 | Bonutti |
| 5,314,438 A | 5/1994 | Shturman |
| 5,360,432 A | 11/1994 | Shturman |
| 5,546,948 A | 8/1996 | Hamm et al. |

(Continued)

FOREIGN PATENT DOCUMENTS

CA 2299997 A1 9/2000

*Primary Examiner* — Ashley L Fishback
(74) *Attorney, Agent, or Firm* — Dinsmore & Shohl LLP

(57) ABSTRACT

A catheter assembly is provided that has a core wire that is at least partially disposed within a lumen of an elongate body including a proximal terminus and a distal terminus of the core wire. The catheter assembly also has a sonic connector at the proximal terminus of the core wire and a tip member at the distal terminus of the core wire. The sonic connector is configured to connect to an ultrasound transducer. The tip member is directly attached to the core wire. The tip member has a cavitation-induced exposed surface. The cavitation-induced exposed surface is configured to introduce a plurality of nanocavities upon exposure of the tip member to a vibrational energy received from the core wire via the sonic connector.

20 Claims, 7 Drawing Sheets

(56) References Cited

U.S. PATENT DOCUMENTS

Figure 1:
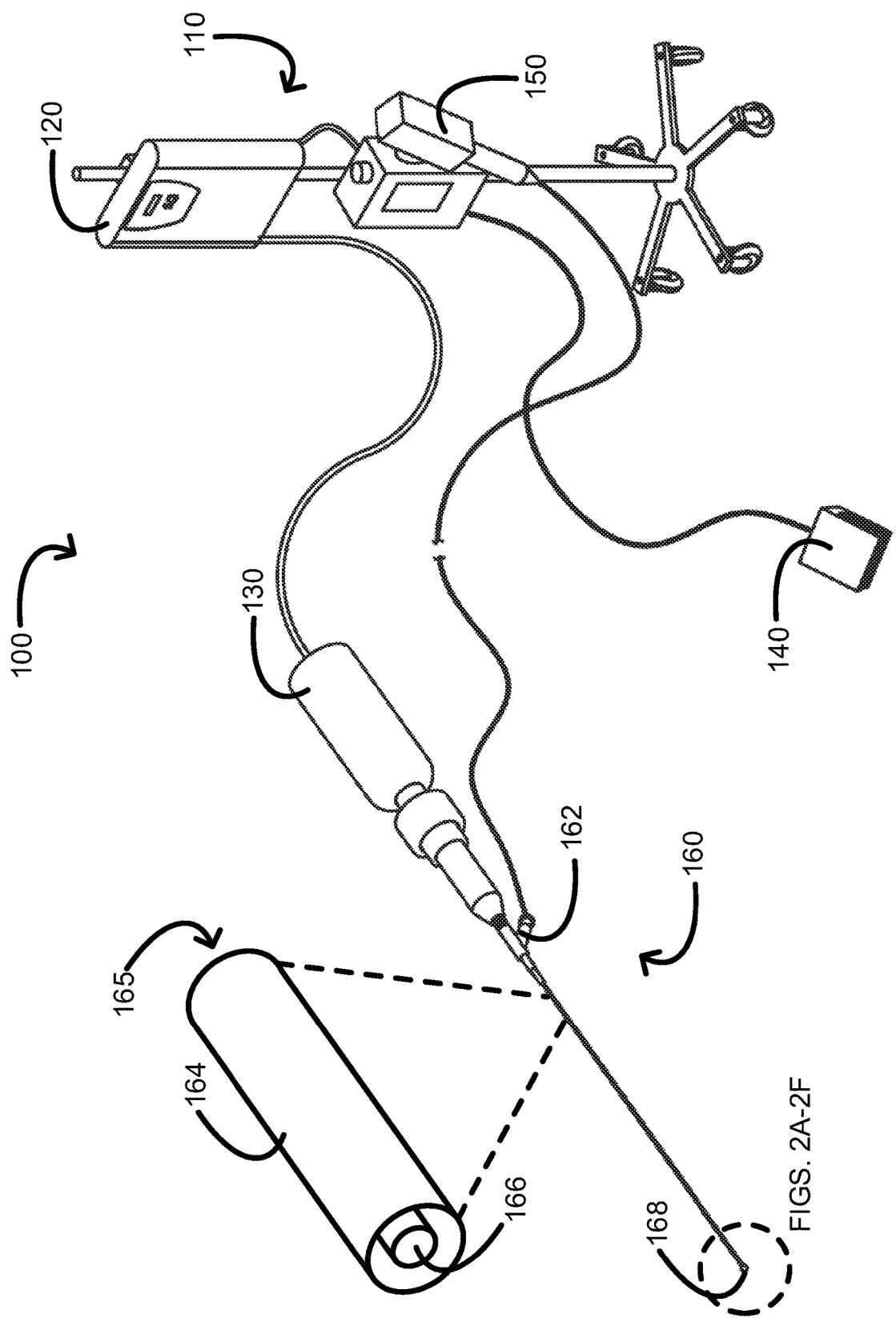

| | | |
|---|---|---|
| 6,241,703 B1 | 6/2001 | Levin et al. |
| 6,423,026 B1 | 7/2002 | Gesswein et al. |
| 7,597,703 B2 | 10/2009 | Sater |
| 2003/0191474 A1 | 10/2003 | Cragg et al. |
| 2008/0287804 A1 | 11/2008 | Nita |
| 2010/0036410 A1 | 2/2010 | Krolik et al. |
| 2011/0196287 A1 | 8/2011 | Fortson et al. |
| 2014/0107709 A1 | 4/2014 | Schmitz et al. |
| 2014/0288583 A1 | 9/2014 | Stinis | ced
ULTRASONICALLY FLARED MEDICAL-DEVICE COMPONENTS AND METHODS THEREOF

PRIORITY

This application is a continuation of U.S. patent application Ser. No. 16/346,694, filed May 1, 2019, now U.S. Pat. No. 11,331,114, which is a U.S. national phase of International Application No. PCT/US2017/061462, filed Nov. 14, 2017, which claims the benefit of priority to U.S. Provisional Patent Application No. 62/427,146, filed Nov. 28, 2016, each of which is incorporated by reference in its entirety herein.

FIELD

This application generally relates to ultrasonically flared medical-device components and methods thereof. In some embodiments, for example, the medical-device component is a flared tip member of an atherectomy catheter for ultrasound-based atherectomy of one or more intravascular lesions.

BACKGROUND

Atherosclerosis is characterized by one or more intravascular lesions formed in part of plaque including blood borne substances such as fat, cholesterol, and calcium. An intravascular lesion such as an arterial lesion can form on a wall of an arterial lumen and build out across the lumen to an opposite wall thereof. A last point of patency often occurs at a boundary between the arterial lesion and the opposite wall of the arterial lumen.

Surgical procedures for atherosclerosis such as atherectomy can be used to restore patency and blood flow lost to the one or more intravascular lesions. Ultrasound-based atherectomy is a promising surgical procedure for atherosclerosis; however, certain components of medical devices for ultrasound-based atherectomy are expected to be adversely affected by the ultrasound used to effect the ultrasound-based atherectomy. Accordingly, there is a need to control adverse effects to such medical-device components. Provided herein in some embodiments are ultrasonically flared medical-device components and methods that address the foregoing.

SUMMARY

Provided herein in some embodiments is a catheter including a core wire, a sonic connector at a proximal terminus of the core wire, and a tip member at a distal terminus of the core wire. The core wire can be at least partially disposed within a lumen of an elongate body. The sonic connector can be configured to couple to an ultrasound-producing mechanism. The tip member can be welded to the core wire at one or more weld locations between the tip member and the core wire, and the tip member can flare from the core wire at one or more weld-free locations between the tip member and the core wire. The manner in which the tip member flares from the core wire at the one or more weld-free locations is characteristic of ultrasonic activation of the tip member.

These and other features of the concepts provided herein may be better understood with reference to the drawings, description, and appended claims.

DRAWINGS

FIG. 1 provides a schematic illustrating an ultrasound-based atherectomy system in accordance with some embodiments.

Figure 2A:
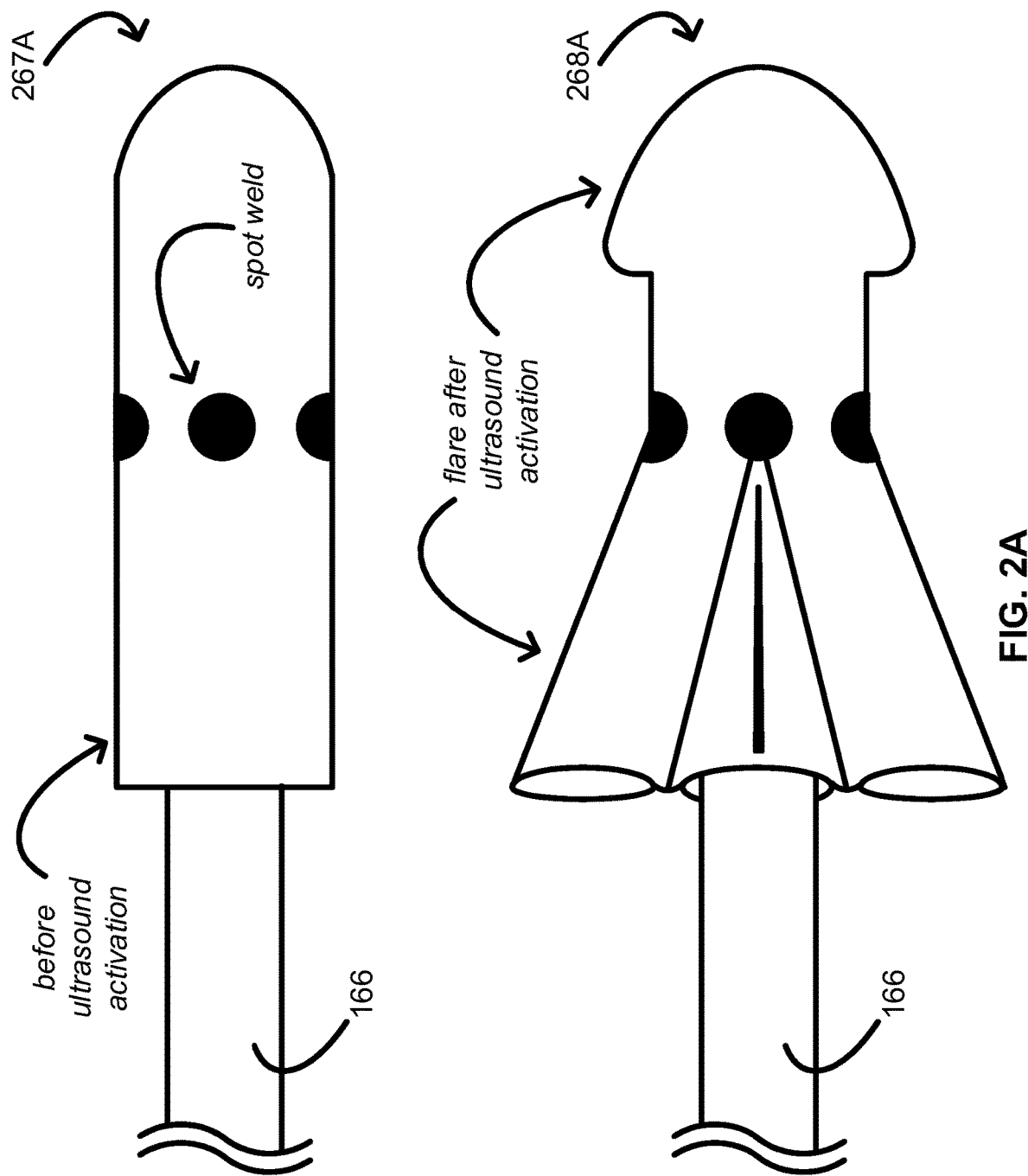

FIG. 2A provides a schematic illustrating a flared tip member in accordance with some embodiments.

Figure 2B:
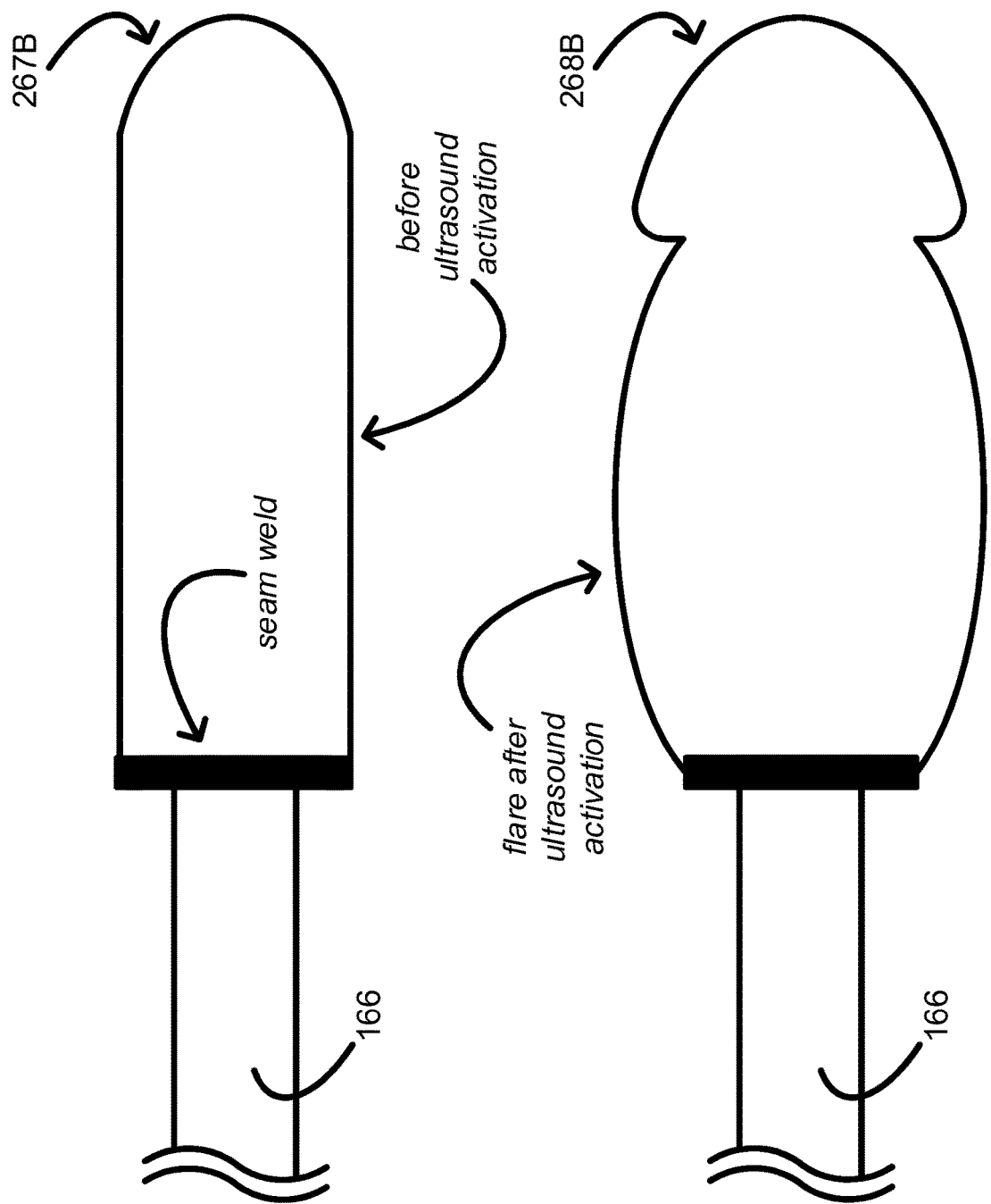

FIG. 2B provides a schematic illustrating a flared tip member in accordance with some embodiments.

Figure 2C:
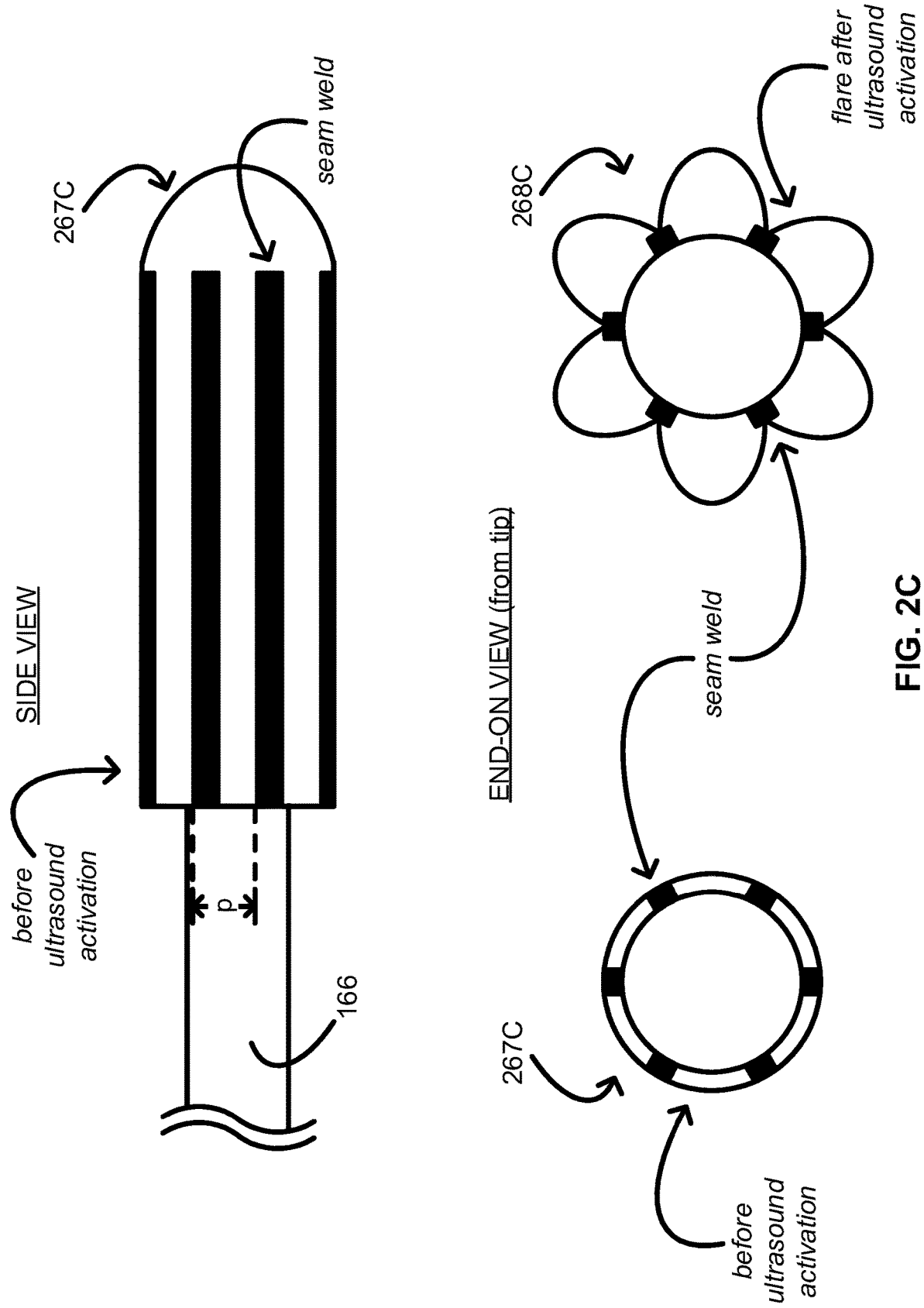

FIG. 2C provides a schematic illustrating a flared tip member in accordance with some embodiments.

Figure 2D:
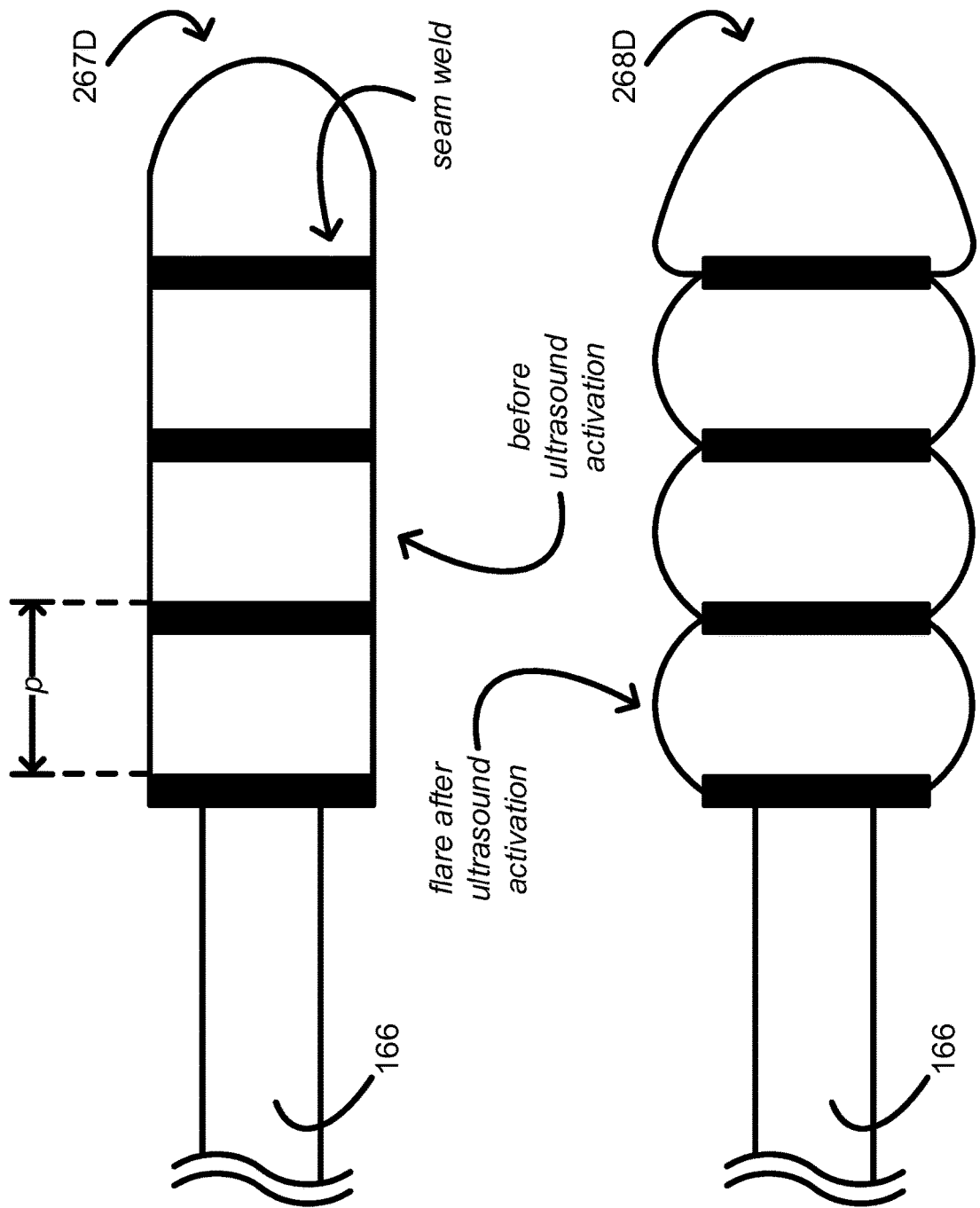

FIG. 2D provides a schematic illustrating a flared tip member in accordance with some embodiments.

Figure 2E:
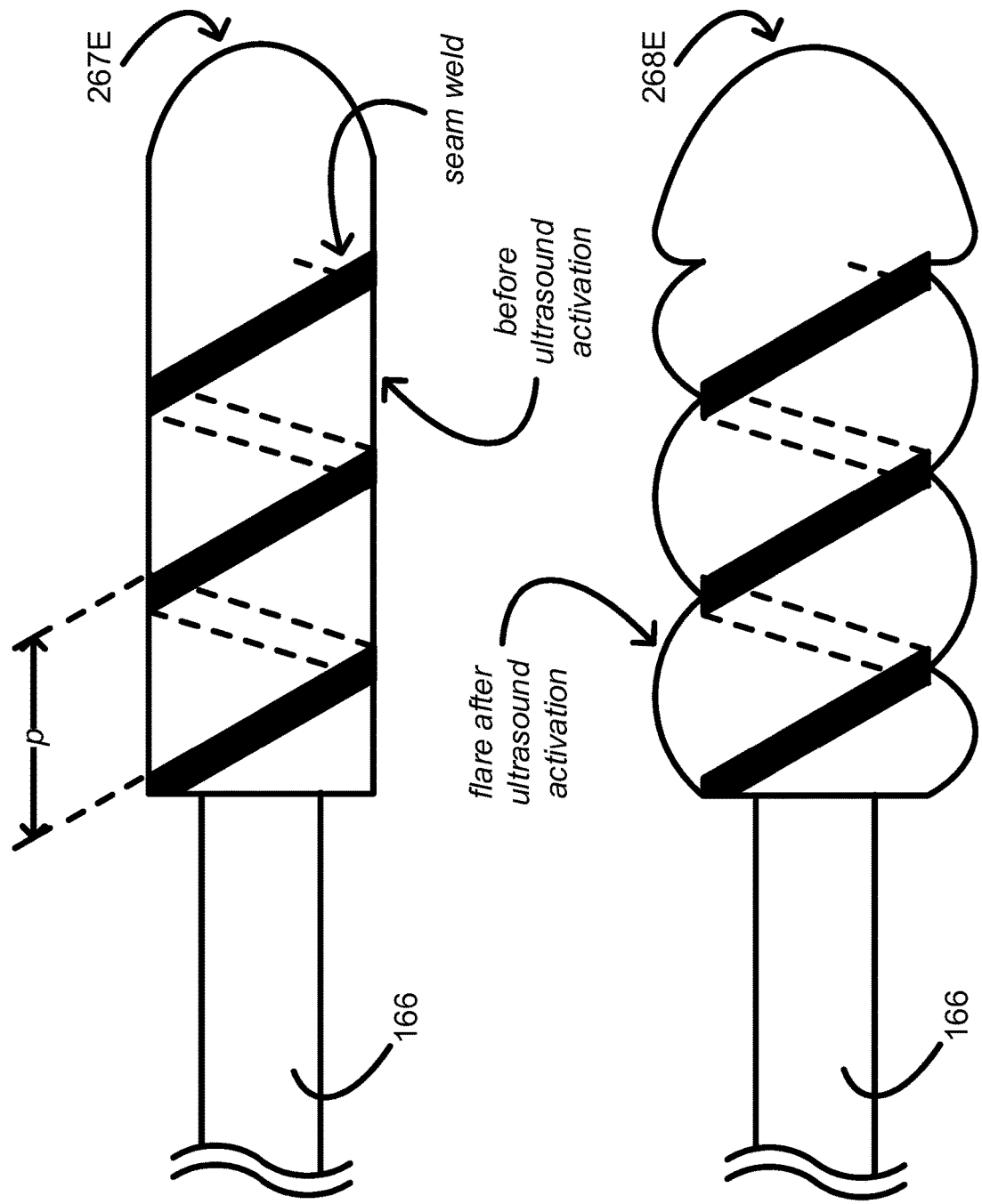

FIG. 2E provides a schematic illustrating a flared tip member in accordance with some embodiments.

Figure 2F:
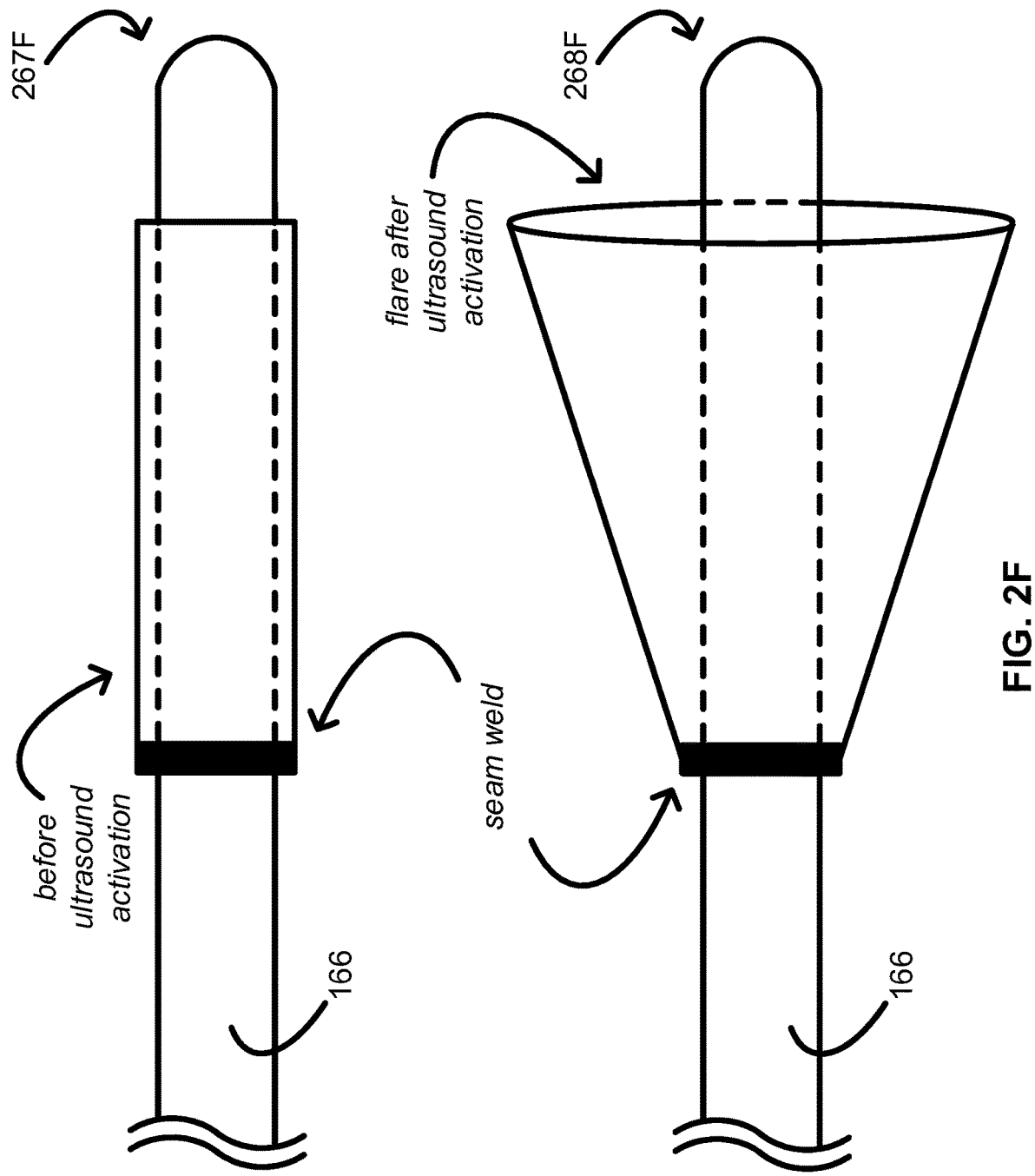

FIG. 2F provides a schematic illustrating a flared tip member in accordance with some embodiments.

DESCRIPTION

Before some particular embodiments are provided in greater detail, it should be understood that the particular embodiments provided herein do not limit the scope of the concepts provided herein. It should also be understood that a particular embodiment provided herein can have features that can be readily separated from the particular embodiment and optionally combined with or substituted for features of any of a number of other embodiments provided herein.

Regarding terminology used herein, it should also be understood the terminology is for the purpose of describing some particular embodiments, and the terminology does not limit the scope of the concepts provided herein. Unless indicated otherwise, ordinal numbers (e.g., first, second, third, etc.) are used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. It should also be understood that, unless indicated otherwise, any labels such as "left," "right," "front," "back," "top," "bottom," "forward," "reverse," "clockwise," "counter clockwise," "up," "down," or other similar terms such as "upper," "lower," "aft," "fore," "vertical," "horizontal," "proximal," "distal," and the like are used for convenience and are not intended to imply, for example, any particular fixed location, orientation, or direction. Instead, such labels are used to reflect, for example, relative location, orientation, or directions. It should also be understood that the singular forms of "a," "an," and "the" include plural references unless the context clearly dictates otherwise.

Unless defined otherwise, all technical and scientific terms used herein have the same meaning as commonly understood those of ordinary skill in the art.

Atherosclerosis is characterized by one or more intravascular lesions formed in part of plaque including blood borne substances such as fat, cholesterol, and calcium. An intravascular lesion such as an arterial lesion can form on a wall of an arterial lumen and build out across the lumen to an opposite wall thereof. A last point of patency often occurs at a boundary between the arterial lesion and the opposite wall of the arterial lumen.

Surgical procedures for atherosclerosis such as atherectomy can be used to restore patency and blood flow lost to the one or more intravascular lesions. Ultrasound-based atherectomy is a promising surgical procedure for atherosclerosis; however, certain components of medical devices for ultrasound-based atherectomy are expected to be adversely affected by the ultrasound used to effect the ultrasound-based atherectomy. For example, an insufficiently attached tip member to a core wire of an ultrasound-based atherectomy catheter is expected to cause unwanted flaring in the tip member by the ultrasound used to effect the ultrasound-based atherectomy. Accordingly, there is a need to control adverse effects to such medical-device components including the unwanted flaring in tip members. Provided herein in some embodiments are ultrasonically flared medical-device components and methods that address the foregoing.

For example, provided herein in some embodiments is a catheter including a core wire, a sonic connector at a proximal terminus of the core wire, and a tip member at a distal terminus of the core wire. The core wire can be at least partially disposed within a lumen of an elongate body. The sonic connector can be configured to couple to an ultrasound-producing mechanism. The tip member can be welded to the core wire at one or more weld locations between the tip member and the core wire, and the tip member can flare from the core wire at one or more weld-free locations between the tip member and the core wire. The manner in which the tip member can flare from the core wire at the one or more weld-free locations is characteristic of ultrasonic activation of the tip member.

FIG. 1 provides a schematic illustrating an ultrasound-based atherectomy system 100 in accordance with some embodiments. Ultrasonically flared medical-device components such as ultrasonically flared tip members can be used in such a system.

As shown in FIG. 1, the system 100 can include a console 110. The console 110 provides a system operator an instrument for monitoring and controlling the system 100 and various sub-systems and functions thereof. The console 110 can include an ultrasound-producing mechanism including an ultrasound generator 120 and an ultrasound transducer 130. The ultrasound-producing mechanism can be configured to convert an electric current into a vibrational energy. For example, the ultrasound generator 120 can be configured to convert an alternating electric current (e.g., a current associated with mains electricity) into a high-frequency current (e.g., a current with a frequency commensurate with the operating frequency of the ultrasound transducer 130), and the ultrasound transducer 130, in turn, can be configured to convert the high-frequency current into the vibrational energy (e.g., >20 kHz such as 20.5 kHz±500 Hz).

In some embodiments, the console 110 can further include a foot switch 140 configured to activate and deactivate the system 100 such as activate and deactivate a core wire of a catheter assembly 160. For example, when the system 100 is powered on but not activated, the foot switch 140 can be used to activate the system 100, thereby activating the core wire of the catheter assembly 160. When the system 100 is powered on and activated, the foot switch 140 can be used to deactivate the system 100, thereby deactivating the core wire of the catheter assembly 160.

In some embodiments, the console 110 can further include an injector 150 configured to inject an irrigant into an optional irrigation lumen 162 of the catheter assembly 160. The irrigant can be, for example, sterile saline for irrigating an anatomical area undergoing an intravascular lesion-modification procedure (e.g., ultrasound-based atherectomy), cooling the core wire of the catheter assembly 160, or a combination thereof.

In some embodiments, the console 110 can further include the foot switch 140 and the injector 150. In such embodiments, the foot switch 140 can be further configured to activate and deactivate the injector 150 when the system 100 is respectively activated and deactivated with the foot switch 140.

As shown in FIG. 1, the system 100 can also include a catheter assembly 160. The catheter assembly 160 can include an elongate body 164 including an elongate-body lumen 165 and a core wire 166 at least partially disposed within the elongate-body lumen 165. The core wire 166 can include a proximal portion and a distal portion of the core wire 166. A proximal terminus of the proximal portion of the core wire 166 can be coupled to the ultrasound-producing mechanism by a sonic connector (not shown) to the ultrasound transducer 130 or an intervening ultrasonic horn. A distal terminus of the distal portion of the core wire 166 can be coupled to a tip member or flared tip member 168 such as any one of the flared tip members shown in FIGS. 2A-2F.

A working length of the distal portion of the core wire 166 beyond the elongate-body lumen 165 can be configured for displacement to effect intravascular lesion modification by ultrasound-based atherectomy. The displacement can be longitudinal, transverse, or longitudinal and transverse displacement in accordance with a profile of the core wire 166 and the vibrational energy (e.g., >20 kHz such as 20.5 kHz±500 Hz). Longitudinal displacement of the working length of the core wire 166 can result in micromotion such as cavitation, and transverse displacement of the working length of the core wire 166 can result in macromotion. The micromotion can be used to cross intravascular lesions. The macromotion coupled with the micromotion can be used to ablate intravascular lesions, thereby breaking the lesions into minute fragments and restoring patency and blood flow. The working length of the core wire 166 can range between about 5 and 200 mm, including about 5 and 100 mm or 100 and 200 mm.

FIGS. 2A-2F provide a schematics illustrating flared tip members in accordance with some embodiments.

As provided herein, the flared tip member 168 can be coupled to the distal terminus of the distal portion of the core wire 166, and the flared tip member 168 can be, but is not limited to, any one of the flared tip members shown in FIGS. 2A-2F or a modification thereof including combinations of any two or more of the flared tip members shown in FIGS. 2A-2F.

A core wire such as the core wire 166 can be inserted into an unflared tip member resulting in a wire-tip assembly with an engineering fit between the core wire 166 and the unflared tip member selected from a clearance fit, a transition fit, and an interference fit. The clearance fit is a fairly loose fit that enables the core wire 166 to freely rotate or slide within the unflared tip member; the transition fit firmly holds the core wire 166 in place within the unflared tip member, but not so firmly that the core wire 166 cannot be removed from the unflared tip member; and the interference fit securely holds the core wire 166 in place within the unflared tip member such that the core wire 166 cannot be removed from the unflared tip member without damaging the core wire 166 or the unflared tip member.

One or more welds such as one or more spot welds, seam welds, or spot welds and seam welds can be used to secure, and, thereby, couple the unflared tip member to the core wire 166 resulting in a welded wire-tip assembly. The one or more welds can be laser welds, which can provide narrow, deep welds at high speed. In addition, the one or more welds can be used as guides for shaping the unflared tip member of the welded wire-tip assembly into a flared tip member such as the flared tip member 168 that can be exploited for ultrasound-based atherectomy.

The unflared tip member can be shaped into the flared tip member 168 through ultrasound activation of the welded wire-tip assembly, wherein portions of the unflared tip member welded to the core wire 166 (i.e., weld locations of the tip member) remain substantially unaffected with respect to outwardly expanding or flaring under the ultrasound activation, and wherein portions of the unflared tip member not welded to the core wire 166 (i.e., weld-free locations of the tip member) outwardly expand or flare under the ultrasound activation. Thus, the manner in which the flared tip member 168 can flare from the core wire 166 at the one or more weld-free locations is characteristic of ultrasonic activation. A further characteristic of ultrasonic activation can include cavitation-induced surface modification such as introduction of nanocavities or nanopores in an exposed surface of the flared tip member 168, wherein the nanocavities or nanopores are no more than 100 nm in in average diameter, including no more than 50 nm, such as no more than 25 nm, for example, no more than 10 nm. The ultrasound activation can include, but is not limited to, exposure of the welded wire-tip assembly to a vibrational energy greater than about 20 kHz (e.g., 20.5 kHz±500 Hz) for a period of time (e.g., 5 minutes or less) sufficient for substantially complete flaring. Not only does the ultrasound activation shape the unflared tip member into the flared tip member 168, but the ultrasound activation ensures the flared tip member 168 remains substantially unaffected by further ultrasound activation. In other words, the flared tip member 168 does not become more flared in weld-free locations under ultrasound-based atherectomy conditions.

FIG. 2A provides a schematic illustrating a flared tip member 268A in accordance with some embodiments. As shown, the flared tip member 268A can be coupled to the core wire 166. Prior to ultrasound activation, an unflared tip member 267A of a welded wire-tip assembly can be approximately bullet shaped with one or more welds such as the spot welds shown in FIG. 2A, which spot welds can be two or four (or more) opposing spot welds about a medial portion of the unflared tip member 267A. Subsequent to ultrasound activation, the flared tip member 268A can be flared as shown in one or more weld-free locations about the flared tip member 268A. For example, the flared tip member 268A can flare from the core wire 166 at the one or more weld-free locations in a number of longitudinal fins, wherein each fin of the number of fins can be minimally flared near a spot weld about a medial portion of the flared tip member 268A and maximally flared farthest from the spot weld.

FIG. 2B provides a schematic illustrating a flared tip member 268B in accordance with some embodiments. As shown, the flared tip member 268B can be coupled to the core wire 166. Prior to ultrasound activation, an unflared tip member 267B of a welded wire-tip assembly can be approximately bullet shaped with one or more welds such as the seam weld shown in FIG. 2B, which seam weld can be a latitudinal or circumferential weld about a proximal portion of the unflared tip member 267B. Subsequent to ultrasound activation, the flared tip member 268B can be flared as shown in one or more weld-free locations about the flared tip member 268B. For example, the flared tip member 268B can flare from the core wire 166 at the one or more weld-free locations in a circumferential bulge about a medial portion of the flared tip member 268B, wherein the circumferential bulge can be minimally flared near a circumferential seam weld about a proximal end of the flared tip member 268B and maximally flared about a middle of the medial portion.

FIG. 2C provides a schematic illustrating a flared tip member 268C in accordance with some embodiments. As shown, the flared tip member 268C can be coupled to the core wire 166. Prior to ultrasound activation, an unflared tip member 267C of a welded wire-tip assembly can be approximately bullet shaped with one or more welds such as the seam welds shown in FIG. 2C, which seam welds can include a number of longitudinal seam welds over a medial-to-proximal portion of the unflared tip member 267C. The number of longitudinal seam welds can include a latitudinally or circumferentially measured pitch p. Subsequent to ultrasound activation, the flared tip member 268C can be flared as shown in one or more weld-free locations about the flared tip member 268C. For example, the flared tip member 268C can flare from the core wire 166 at the one or more weld-free locations in a number of longitudinal bulges, wherein each bulge of the number of bulges can be minimally flared near a longitudinal seam weld and maximally flared between the longitudinal seam weld and an adjacent longitudinal seam weld.

FIG. 2D provides a schematic illustrating a flared tip member 268D in accordance with some embodiments. As shown, the flared tip member 268D can be coupled to the core wire 166. Prior to ultrasound activation, an unflared tip member 267D of a welded wire-tip assembly can be approximately bullet shaped with one or more welds such as the seam welds shown in FIG. 2D, which seam welds can include a number of latitudinal or circumferential seam welds over a medial-to-proximal portion of the unflared tip member 267D. The number of latitudinal or circumferential seam welds can include a longitudinally measured pitch p. Subsequent to ultrasound activation, the flared tip member 268D can be flared as shown in one or more weld-free locations about the flared tip member 268D. For example, the flared tip member 268D can flare from the core wire 166 at the one or more weld-free locations in a number of circumferential bulges, wherein each bulge of the number of bulges can be minimally flared near a circumferential seam weld and maximally flared between the circumferential seam weld and an adjacent circumferential seam weld.

FIG. 2E provides a schematic illustrating a flared tip member 268E in accordance with some embodiments. As shown, the flared tip member 268E can be coupled to the core wire 166. Prior to ultrasound activation, an unflared tip member 267E of a welded wire-tip assembly can be approximately bullet shaped with one or more welds such as the seam weld shown in FIG. 2E, which seam weld can include a helical seam weld over a medial-to-proximal portion of the unflared tip member 267E. The helical seam weld can include a longitudinally measured pitch p, which pitch can be defined as a longitudinal distance over the unflared tip member 267E of one complete turn of the helical seam. Subsequent to ultrasound activation, the flared tip member 268E can be flared as shown in one or more weld-free locations about the flared tip member 268E. For example, the flared tip member 268E can flare from the core wire 166 at the one or more weld-free locations in a helical bulge, wherein the helical bulge can be minimally flared near a helical seam weld about one turn of the helical seam weld and maximally flared between the helical seam weld about the one turn of the helical seam weld and the helical seam weld about an adjacent turn of the helical seam weld.

FIG. 2F provides a schematic illustrating a flared tip member 268F in accordance with some embodiments. As shown, the flared tip member 268F can be coupled to the core wire 166. Prior to ultrasound activation, an unflared tip member 267F of a welded wire-tip assembly can be approximately shaped as shown in FIG. 2F with one or more welds such as the latitudinal or circumferential seam weld over a proximal portion of the unflared tip member 267F. Subsequent to ultrasound activation, the flared tip member 268F can be flared as shown in one or more weld-free locations about the flared tip member 268F. For example, the flared tip member 268F can flare from the core wire 166 at the one or more weld-free locations in a conical flare, wherein the conical flare can be minimally flared near a circumferential seam weld about a proximal end of the flared tip member 268F and maximally flared about a distal end of the flared tip member 268F. Furthermore, a distal end of the core wire 166 can optionally extend past the distal end of the flared tip member 268F.

As such, provided herein in some embodiments is a catheter including a tip member at a distal terminus of a core wire configured for ultrasound-based atherectomy of one or more intravascular lesions. The tip member can be welded to the core wire at one or more weld locations between the tip member and the core wire, and the tip member can flare from the core wire at one or more weld-free locations between the tip member and the core wire.

In such embodiments, the tip member can flare from the core wire at the one or more weld-free locations shown in FIG. 2A. For example, the one or more weld-free locations can include a number of longitudinal fins. In such embodiments, the tip member can flare from the core wire at the one or more weld-free locations shown in FIG. 2B. For example, the one or more weld-free locations can include a circumferential bulge about a medial portion of the tip member. In such embodiments, the tip member can flare from the core wire at the one or more weld-free locations shown in FIG. 2C. For example, the one or more weld-free locations can include a number of longitudinal bulges. In such embodiments, the tip member can flare from the core wire at the one or more weld-free locations shown in FIG. 2D. For example, the one or more weld-free locations can include a number of circumferential bulges. In such embodiments, the tip member can flare from the core wire at the one or more weld-free locations shown in FIG. 2E. For example, the one or more weld-free locations can include a helical bulge. In such embodiments, the tip member can flare from the core wire at the one or more weld-free locations shown in FIG. 2F. For example, the one or more weld-free locations can include a conical flare, wherein a distal end of the core wire can optionally extend past the distal end of the tip member. In such embodiments, the catheter can be configured for ultrasound-based atherectomy of one or more intravascular lesions with the tip member.

Also provided herein in some embodiments is a catheter including a core wire, a sonic connector at a proximal terminus of the core wire, and a tip member at a distal terminus of the core wire. The core wire can be at least partially disposed within a lumen of an elongate body. The sonic connector can be configured to couple to an ultrasound-producing mechanism. The tip member can be welded to the core wire at one or more weld locations between the tip member and the core wire, and the tip member can flare from the core wire at one or more weld-free locations between the tip member and the core wire.

In such embodiments, the one or more weld locations can include welds selected from spot welds, seam welds, or a combination of spot welds and seam welds. In such embodiments, the manner in which the tip member can flare from the core wire at the one or more weld-free locations is characteristic of ultrasonic activation of the tip member. In such embodiments, the tip member can flare from the core wire at the one or more weld-free locations shown in FIG. 2A. For example, the one or more weld-free locations can include a number of longitudinal fins, wherein each fin of the number of fins can be minimally flared near a spot weld about a medial portion of the tip member and maximally flared farthest from the spot weld. In such embodiments, the tip member can flare from the core wire at the one or more weld-free locations shown in FIG. 2B. For example, the one or more weld-free locations can include a circumferential bulge about a medial portion of the tip member, wherein the circumferential bulge can be minimally flared near a circumferential seam weld about a proximal end of the tip member and maximally flared about a middle of the medial portion. In such embodiments, the tip member can flare from the core wire at the one or more weld-free locations shown in FIG. 2C. For example, the one or more weld-free locations can include a number of longitudinal bulges, wherein each bulge of the number of bulges can be minimally flared near a longitudinal seam weld and maximally flared between the longitudinal seam weld and an adjacent longitudinal seam weld. In such embodiments, the tip member can flare from the core wire at the one or more weld-free locations shown in FIG. 2D. For example, the one or more weld-free locations can include a number of circumferential bulges, wherein each bulge of the number of bulges can be minimally flared near a circumferential seam weld and maximally flared between the circumferential seam weld and an adjacent circumferential seam weld. In such embodiments, the tip member can flare from the core wire at the one or more weld-free locations shown in FIG. 2E. For example, the one or more weld-free locations can include a helical bulge, wherein the helical bulge can be minimally flared near a helical seam weld about one turn of the helical seam weld and maximally flared between the helical seam weld about the one turn of the helical seam weld and the helical seam weld about an adjacent turn of the helical seam weld. In such embodiments, the tip member can flare from the core wire at the one or more weld-free locations shown in FIG. 2F. For example, the one or more weld-free locations can include a conical flare, wherein the conical flare can be minimally flared near a circumferential seam weld about a proximal end of the tip member and maximally flared about a distal end of the tip member, and wherein a distal end of the core wire can extend past the distal end of the tip member. In such embodiments, the catheter can be configured for ultrasound-based atherectomy of one or more intravascular lesions with the tip member.

Also provided herein in some embodiments is a system including a catheter assembly and a console. The catheter assembly can include a core wire, a sonic connector at a proximal terminus of the core wire, and a tip member at a distal terminus of the core wire. The core wire can be at least partially disposed within a lumen of an elongate body. The tip member can be welded to the core wire at one or more weld locations between the tip member and the core wire, and the tip member can flare from the core wire at one or more weld-free locations between the tip member and the core wire. The console can include an ultrasound-producing mechanism configured to convert an electric current into a vibrational energy. The sonic connector of the core wire can be configured to couple to the ultrasound-producing mechanism for ultrasound-based atherectomy of one or more intravascular lesions with the tip member of the core wire.

In such embodiments, the ultrasound-producing mechanism can include an ultrasonic generator, an ultrasonic transducer, and an ultrasonic horn. The ultrasonic generator can be configured to convert an alternating electric current into a high-frequency current. The ultrasonic transducer can be configured to convert the high-frequency current into the vibrational energy. The ultrasonic horn can be configured to augment an amplitude of the vibrational energy. The sonic connector of the core wire can be configured to couple to the ultrasonic horn. In such embodiments, the one or more weld locations can include welds selected from spot welds, seam welds, or a combination of spot welds and seam welds. The tip member can flare from the core wire at the one or more weld-free locations as shown in any figure of FIGS. 2A-2F. For example, the tip member can flare from the core wire in a number of longitudinal fins, a circumferential bulge, a number of longitudinal bulges, a number of circumferential bulges, a helical bulge, or a conical flare.

While some particular embodiments have been provided herein, and while the particular embodiments have been provided in some detail, it is not the intention for the particular embodiments to limit the scope of the concepts presented herein. Additional adaptations and/or modifications can appear to those of ordinary skill in the art, and, in broader aspects, these adaptations and/or modifications are encompassed as well. Accordingly, departures may be made from the particular embodiments provided herein without departing from the scope of the concepts provided herein.

What is claimed is:

1. A catheter assembly comprising:
    a core wire at least partially disposed within a lumen of an elongate body including a proximal terminus and a distal terminus of the core wire;
    a sonic connector at the proximal terminus of the core wire, the sonic connector configured to connect to an ultrasound transducer; and
    a tip member at the distal terminus of the core wire, the tip member directly attached to the core wire, the tip member having a cavitation-induced exposed surface,
    wherein the cavitation-induced exposed surface is configured to introduce a plurality of nanocavities upon exposure of the tip member to a vibrational energy received from the core wire via the sonic connector.

2. The catheter assembly of claim 1, further comprising a weld directly attaching the tip member to the core wire, wherein the weld is configured to permit the vibrational energy to pass from the core wire to the tip member.

3. The catheter assembly of claim 1, wherein the plurality of nanocavities has an average diameter of no more than 100 nm.

4. The catheter assembly of claim 1, wherein the plurality of nanocavities has an average diameter of no more than 25 nm.

5. The catheter assembly of claim 1, wherein the plurality of nanocavities has an average diameter of no more than 10 nm.

6. The catheter assembly of claim 1, wherein the catheter assembly is configured for ultrasound-based atherectomy of one or more intravascular lesions with the tip member.

7. The catheter assembly of claim 1, wherein the tip member is directly attached to the core wire at least two weld locations, the tip member having a space on the tip member located between a pair of two adjacent weld locations, the space of the tip member is configured to flare from the core wire upon exposure of the tip member to ultrasonic vibrational energy.

8. The catheter assembly of claim 7, wherein the ultrasonic vibrational energy is greater than 20 kHz and delivered for a maximum period of time of five minutes.

9. The catheter assembly of claim 7, wherein the at least two weld locations include welds selected from spot welds, seam welds, or a combination of spot welds and seam welds.

10. A catheter assembly, comprising:
    a tip member at a distal terminus of a core wire configured for ultrasound-based atherectomy of one or more intravascular lesions, the tip member directly attached to the core wire, the tip member having a cavitation-induced exposed surface; and
    a weld directly connecting the tip member to the core wire at a weld location, the cavitation-induced exposed surface of the tip member is configured to flare away from the core wire upon exposure of the tip member to ultrasonic vibrations.

11. The catheter assembly of claim 10, wherein the weld is a spot weld, the weld location is at a medial portion of the tip member, the tip member is configured to flare from the core wire in a plurality of longitudinal fins, and wherein each fin of the plurality of longitudinal fins is minimally flared near the spot weld about the medial portion of the tip member and maximally flared farthest from the spot weld.

12. The catheter assembly of claim 10, wherein the weld comprises a circumferential seam weld about a proximal end of the tip member, the tip member is configured to flare from the core wire in a circumferential bulge about a medial portion of the tip member.

13. The catheter assembly of claim 12, wherein the circumferential bulge is minimally flared near the circumferential seam weld about the proximal end of the tip member and maximally flared about a middle of the medial portion.

14. The catheter assembly of claim 10, wherein the weld comprises a longitudinal seam weld and an adjacent longitudinal seam weld, the tip member is configured to flare from the core wire in a plurality of longitudinal bulges.

15. The catheter assembly of claim 14, wherein each longitudinal bulge of the plurality of longitudinal bulges is minimally flared near the longitudinal seam weld and maximally flared along a longitudinally-shaped space between the longitudinal seam weld and an adjacent longitudinal seam weld.

16. The catheter assembly of claim 10, wherein the weld is a helical seam weld at the weld location, wherein the tip member is configured to flare from the core wire in a helical bulge, and wherein the helical bulge is minimally flared near the helical seam weld about one turn of the helical seam weld and maximally flared between the helical seam weld about the one turn of the helical seam weld and the helical seam weld about an adjacent turn of the helical seam weld.

17. The catheter assembly of claim 10, wherein the weld directly attaches the tip member to the core wire at the weld location, wherein the weld is configured to permit the vibrational energy to pass from the core wire to the tip member.

18. The catheter assembly of claim 10, wherein the plurality of nanocavities has an average diameter of no more than 100 nm.

19. The catheter assembly of claim 10, wherein the plurality of nanocavities has an average diameter of no more than 25 nm.

20. The catheter assembly of claim 10, wherein the plurality of nanocavities has an average diameter of no more than 10 nm.

* * * * *